(12) United States Patent
Nemeth (10) Patent No.: US 10,834,920 B1
(45) Date of Patent: Nov. 17, 2020

(54) VITRIFICATION STICK WITH BASKET END TIP

(71) Applicant: Lee L. Nemeth, Prospect, CT (US)

(72) Inventor: Lee L. Nemeth, Prospect, CT (US)

( * ) Notice: Subject to any disclaimer, the term of this patent is extended or adjusted under 35 U.S.C. 154(b) by 0 days.

(21) Appl. No.: 16/741,483

(22) Filed: Jan. 13, 2020

(51) Int. Cl.
*A01N 1/02* (2006.01)
*C12M 1/34* (2006.01)

(52) U.S. Cl.
CPC ......... *A01N 1/0268* (2013.01); *A01N 1/0257* (2013.01); *C12M 1/34* (2013.01)

(58) Field of Classification Search
CPC ............................ A01N 1/0257; A01N 1/0268
See application file for complete search history.

(56) References Cited

U.S. PATENT DOCUMENTS

| 2004/0259072 A1 | 12/2004 | Kuwayama et al. | |
| 2008/0038155 A1* | 2/2008 | Chian | A61D 19/024 422/400 |
| 2010/0317108 A1* | 12/2010 | Stojanov | A01N 1/0236 435/374 |
| 2011/0129811 A1* | 6/2011 | Tao | A01N 1/0268 435/1.3 |
| 2011/0275153 A1* | 11/2011 | Butler | A01N 1/0268 435/374 |
| 2016/0174545 A1 | 6/2016 | Parra et al. | |

OTHER PUBLICATIONS

U.S. Appl. No. 16/741,396, filed Jan. 13, 2020, Nemeth.
U.S. Appl. No. 29/720,442, filed Jan. 13, 2020, Nemeth.
Non-Final Office Action dated Mar. 18, 2020 in U.S. Appl. No. 16/741,396.

* cited by examiner

*Primary Examiner* — William H. Beisner
(74) *Attorney, Agent, or Firm* — Ware, Fressola, Maguire & Barber LLP (57) ABSTRACT

The present invention is directed to a vitrification stick for use in the cryopreservation of biological materials, and may include a body having a first portion and a second portion, and a specimen end extending from the second portion of the body, and having a basket end tip formed thereon. The basket end tip may include a peripheral wall enclosing an interior region of the basket end tip, and the interior region may be further enclosed on a first side by a shell connected to the peripheral wall, and the interior region may be open on a second side in a direction towards the specimen end. The shell may include at least one slot formed therein.

17 Claims, 11 Drawing Sheets

VITRIFICATION STICK WITH BASKET END TIP

BACKGROUND OF THE INVENTION

1. Field of the Invention

The present invention is directed to vitrification sticks for use in cryopreservation, and more particularly to a vitrification stick with a basket end tip for use in the cryopreservation of biological materials.

2. Description of Related Art

Cryopreservation involves the process of cooling biological materials, such as organelles, cell, tissues, embryos, extracellular matrix and/or organs, to very low temperatures, for example 77 Kelvin (−196° C.) using liquid nitrogen or 193 Kelvin (−80° C.) using dry ice (solid carbon dioxide). At such low temperatures, any biological and/or chemical activity that may cause damage to the biological material is effectively halted, thereby cryogenically preserving the biological material. One of the main purposes of cryopreservation is to allow for long term storage of biological materials. Such long term storage may include the storage of human or other animal egg cells or embryos for fertilization or implantation at a later time. However, for the purposes of cryopreservation it is necessary to reach low temperatures without causing damage to the biological materials through the formation of ice crystals. This may be accomplished through the use of cryoprotectants and/or rapid cooling of the biological materials to the desired cryopreservation temperature.

Vitrification involves the transformation of a solution comprised of a biological material, such as an egg or an embryo, into a glass-like amorphous solid that is free from any crystalline structure, followed by extremely rapid cooling. Successful vitrification requires preventing the formation of ice crystals within the intracellular liquid of the biological material. This may be accomplished by first dehydrating the biological material through the use of cryoprotectant fluids. The biological material may then be rapidly chilled by a cryogenic fluid such as liquid nitrogen. It is possible that multiple cryoprotectant fluids may need to be used in successive stages in order to effectively dehydrate the biological material without causing damage to the biological material. Furthermore, cryoprotectant fluids may be toxic to the biological materials prior to the vitrification of the biological material, and therefore, the time of exposure of the biological materials to the cryoprotectant fluids must be carefully controlled to avoid damage to the biological materials.

Currently, a biological material that is to be cryopreserved may be disposed upon a vitrification stick, and then the cryoprotectant fluid or series of cryoprotectant fluids may be administered to be biological material to allow for the vitrification process. However, this may be manually performed, and may expose the biological material to variances in procedure time and/or the risk that the biological material will become separated from the vitrification stick and thereby lost. The variances in the procedure time may increase the risk that the biological materials are damaged as a result of the cryopreservation process.

Therefore, there is a need for a vitrification stick that reduces the variables and opportunities for error that may occur during administration of the cryoprotectant fluids to the biological materials that are to be vitrified and cryopreserved.

SUMMARY OF THE INVENTION

The present invention is designed to overcome the above noted limitations that are attendant upon the use of conventional vitrification sticks and, toward this end, it contemplates the provision of a novel vitrification stick.

Accordingly, it is an object of the present invention to provide a vitrification stick for use in the cryopreservation of biological materials.

It is another object of the present invention to provide a vitrification stick that can facilitate the application of cryoprotectants to biological materials.

It is yet another object of the present invention to provide a vitrification stick that includes an enclosure for retention of biological materials during the vitrification and cryopreservation processes.

It is still another object of the present invention to provide a vitrification stick that facilitates consistent processing times of biological materials for cryopreservation.

It is another object of the present invention to provide a vitrification stick that facilitates consistent application of cryoprotectants to biological materials.

It is yet another object of the present invention to provide a vitrification stick that allows biological materials to be submerged in cryoprotectants while reducing the risk that the biological materials will become separated from the vitrification stick.

It is still another object of the present invention to provide a vitrification stick that allows for the immersion of biological materials with cryoprotectants while reducing the risk that the biological materials will become separated from the vitrification stick.

It is another object of the present invention to provide a vitrification stick that facilitates long term cryogenic storage of biological materials.

It is yet another object of the present invention to provide a vitrification stick that allows for application of cryoprotectants to biological materials by submersion, immersion and/or flowing over of the cryoprotectants with the biological materials.

In accordance with an exemplary embodiment of the present invention, a vitrification stick for use in the vitrification and cryopreservation of biological materials is provided that may include a body having a first portion and a second portion, and a specimen end extending from the second portion of the body, and the specimen end may include a basket end tip formed thereon.

In accordance with this and other exemplary embodiments of the present invention, the basket end tip may include a peripheral wall enclosing an interior region of the basket end tip.

In accordance with this and other exemplary embodiments of the present invention, the interior region may be further enclosed on a first side by a shell connected to the peripheral wall, and the interior region may be open on a second side in a direction towards the specimen end.

In accordance with this and other exemplary embodiments of the present invention, the shell may include at least one slot formed therein and the at least one slot may expose the interior region of the basket end tip to an area external to the basket end tip.

In accordance with this and other exemplary embodiments of the present invention, the at least one slot may extend into at least a portion of the peripheral wall.

In accordance with this and other exemplary embodiments of the present invention, the second portion may have a smaller cross-sectional dimensional size than the first portion, and a shoulder may be positioned between the first portion and the second portion.

In accordance with this and other exemplary embodiments of the present invention, the vitrification stick may also include a cap that may include an open end and a closed end, and a plurality of walls defining a hollow interior chamber extending between the open end and the closed end.

In accordance with this and other exemplary embodiments of the present invention, the cap may be dimensioned so as to receive the specimen end and at least a part of the second portion of the body.

In accordance with this and other exemplary embodiments of the present invention, the second portion of the body may include a first rib positioned adjacent to the shoulder and extending at least partially around a perimeter of the second portion, and a second rib positioned adjacent to the specimen end and extending at least partially around the perimeter of the second portion.

In accordance with this and other exemplary embodiments of the present invention, the second portion of the body may include a first rib positioned adjacent to the shoulder and extending at least partially around a perimeter of the second portion, and a second rib positioned adjacent to the specimen end and extending at least partially around the perimeter of the second portion.

In accordance with this and other exemplary embodiments of the present invention, the cap may also include a first groove extending at least partially around the hollow interior chamber, and a second groove extending at least partially around the hollow interior chamber.

In accordance with this and other exemplary embodiments of the present invention, the first groove may be configured for engagement with the first rib and the second rib, and the second groove may be configured for engagement with the second rib, and as a result of the engagement of the second groove with the second rib, the basket end may be sealed within the hollow interior chamber of the cap.

In accordance with this and other exemplary embodiments of the present invention, the vitrification stick may be made from a material selected from the group consisting of polyester, polyolefin, polyethylene, polypropylene, ethylene-vinyl acetate copolymer, styrene resin, polystyrene, polyamide, and medical grade polystyrene crystal.

In accordance with this and other exemplary embodiments of the present invention, the basket end tip may be made of a transparent material.

In accordance with this and other exemplary embodiments of the present invention, the transparent material may be a polymer such as polyester, polyolefin, polyethylene, polypropylene, ethylene-vinyl acetate copolymer, styrene resin, polystyrene, polyamide, and medical grade polystyrene crystal.

In accordance with this and other exemplary embodiments of the present invention, the interior region of the basket end tip may be dimensioned to receive and retain a specimen of biological material, for example a human egg or a human embryo, or an egg or embryo of another animal.

In accordance with this and other exemplary embodiments of the present invention, the interior region may be further enclosed on a first side by a shell connected to the peripheral wall, and the shell may include at least one slot formed therein and the at least one slot exposes the interior region of the basket end tip to an area external to the basket end tip.

In accordance with this and other exemplary embodiments of the present invention, the interior region may be open in a direction towards the specimen end.

In accordance with this and other exemplary embodiments of the present invention, a side of the peripheral wall adjacent to the specimen end has a first height, and a side of the peripheral wall opposite the specimen end has a second height, and the second height may be less than the first height.

In accordance with this and other exemplary embodiments of the present invention, around the circumference of the peripheral wall, the peripheral wall tapers from the first height down to the second height, and then back to the first height.

BRIEF DESCRIPTION OF THE DRAWINGS

For a fuller understanding of the nature and objects of the present invention, reference is made to the following detailed description taken in connection with the accompanying drawings in which.

DETAILED DESCRIPTION

The present invention now will be described more fully hereinafter with reference to the accompanying figures, in which exemplary embodiments of the invention are shown. The invention may, however, be embodied in many different forms and should not be construed as limited to the embodiments set forth herein. Like reference numerals refer to like elements throughout.

Referring now to FIGS. 1-12, therein illustrated is an exemplary embodiment of a vitrification stick, generally referred to by reference numeral 10, for use in the cryopreservation of biological materials. The vitrification stick 10 may include a body 12 and a cap 14 configured for removable engagement with the body 12. The body 12 may have a first portion 16 and a second portion 18, and the second portion 18 may have a smaller cross-sectional dimensional size than the first portion 16. The first portion 16 may include a handle 20, and a shoulder 22 may be positioned between the first portion 16 and the second portion 18, thereby defining the reduction in cross-sectional dimension between the first portion 16 and the second portion 18. The body 12 may have any cross-sectional shape, such as triangular, hexagonal, square, circular, octagonal, or the like, and the first portion 16 and the second portion 18 may have the same cross-sectional shape, or have different cross-sectional shapes. It is understood that if the second portion 18 is to have a smaller cross-sectional dimensional size than the first portion 16 this may also be accomplished through the use of a different cross-sectional shape of the second portion 18 that is cross-sectionally encompassed within the cross-sectional shape of the first portion 16. A specimen end 24 may extend from the second portion 18, and the specimen end 24 may extend from the side of the second portion 18 opposite the side of the second portion 18 adjacent to the first portion 16. The specimen end 24 may have a thin and substantially flexible construction, and may also include a basket end tip 26 formed therein for receipt and retention of a specimen of biological material (not shown), for example a human egg or embryo. The basket end tip 26 may be configured to substantially enclose the specimen to provide for secure retention of the specimen on the specimen end 24. The basket end tip 26 may include a peripheral wall 28 enclosing an interior region 30 of the basket end tip 26. It is understood that the specimen may be placed within and retained in the interior region 30 of the basket end tip 26. The interior region 30 may be substantially enclosed on one side of the basket end tip 26 by a shell 32. The shell 32 is connected to the peripheral wall 28 to at least substantially enclose the one side of the basket end tip 26. One or more slots 34 may be formed in the shell 32 so that at least one opening may be formed in the side of the basket end tip 26 substantially enclosed by the shell 32. The one or more slots 34 may extend into at least a portion of the peripheral wall 28.

Referring again to FIGS. 1-12, the cap 14 may include a plurality of walls 36, a closed end 38 and an open end 40 defining an interior region 42 of the cap 14. The cap 14 may have the same cross-sectional shape as the second portion 18 of the body 12, for example, triangular, hexagonal, square, circular, octagonal, or the like. The interior region 42 is complementarily sized relative to the second portion 18 so that the cap 14 is dimensioned to receive the specimen end 24 and at least a part of the second portion 18 of the body 12 through the open end 38 of the cap 14. The inner cross-sectional size of the cap 14 may be such that at least a part of the second portion 18 of the body 12 may be slidenly received through the open end 40 and within the interior region 42.

Still referring to FIGS. 1-12, a first rib 44 and a second rib 46 may be positioned around the perimeter of the second portion 18 substantially perpendicular to the longitudinal axis of the body 12. The first rib 44 may be positioned substantially adjacent to the shoulder 22, or if no clearly defined shoulder is present between the first portion 16 and the second portion 18, substantially adjacent to the first portion 16. The second rib 46 may be spaced apart from the first rib 44, and positioned on the second portion 18 closer to the specimen end 24 than the first rib 44. Each of the first rib 44 and the second rib 46 extend from the surface of the perimeter of the second portion 18 so that the first rib 44 and the second rib 46 are at least slightly raised relative to the other surfaces of the second portion 18. In order to allow for cooperation between the first rib 44 and the second rib 46 on the second portion 18 and the cap 14, the cap 14 may include a first groove 48 and a second groove 50 formed in at least a portion of the one or more walls 36 facing the interior region 42 of the cap 14. The first rib 44 and the second rib 46 are dimensioned and shaped so as to have a meshing relationship with the first groove 48 and the second groove 50. In other words, the first rib 44 and the second rib 46 are configured to be snuggly removably received within the first groove 48 and the second groove 50. In this manner, the cap 14 may be removably secured to the body 12 of the vitrification stick 10. It is understood that the first rib 44 and second rib 46 may instead be formed on in interior of the cap 14, and the first groove 48 and the second groove 50 may be formed on the second portion 18 of the body 12, so that the same meshing relationship is achieved to removably secure the cap 14 to the body 12. Likewise, it is understood that only one rib may be formed on either the cap 14 or the second portion 18, and a corresponding groove formed in the other component to achieve the same meshing relationship. It is further understood that the cap 14 may also be removably secured to the body 12 through the use of a taper of the second portion 18 and/or the interior region 42 of the cap 14 so that at least a part of the second portion 18 snuggly fit into at least a part of the cap 14.

Figure 1:
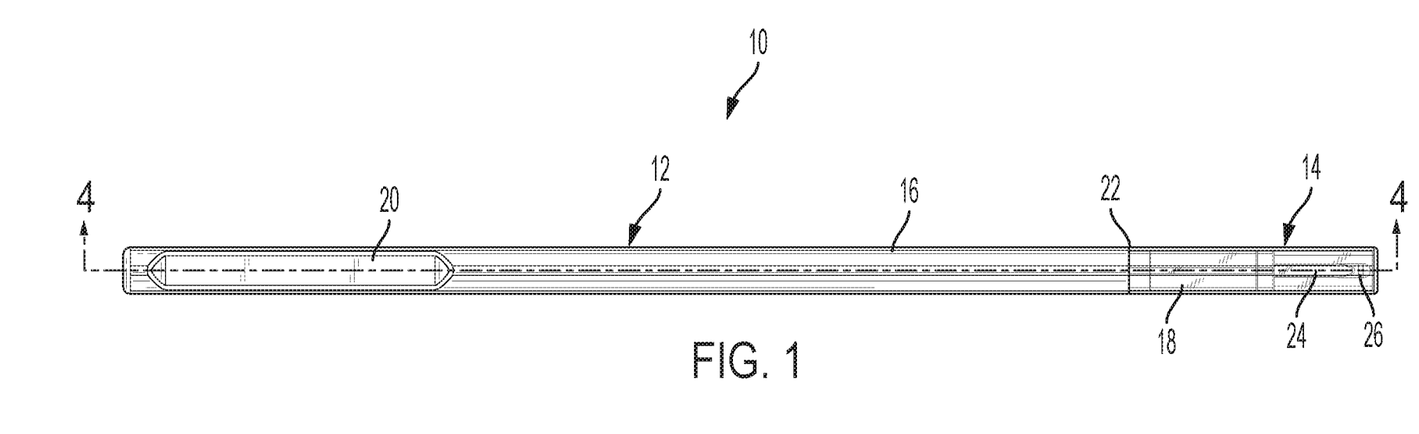
FIG. 1 is a top plan view of an exemplary vitrification stick according to an aspect of the present invention.
Figure 2:
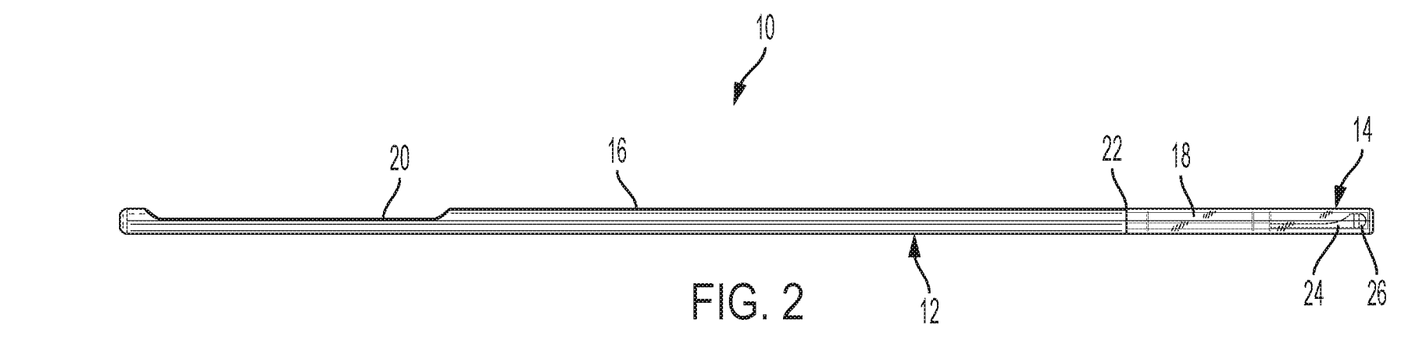
FIG. 2 is a right side view of the exemplary vitrification stick.
Figure 3:
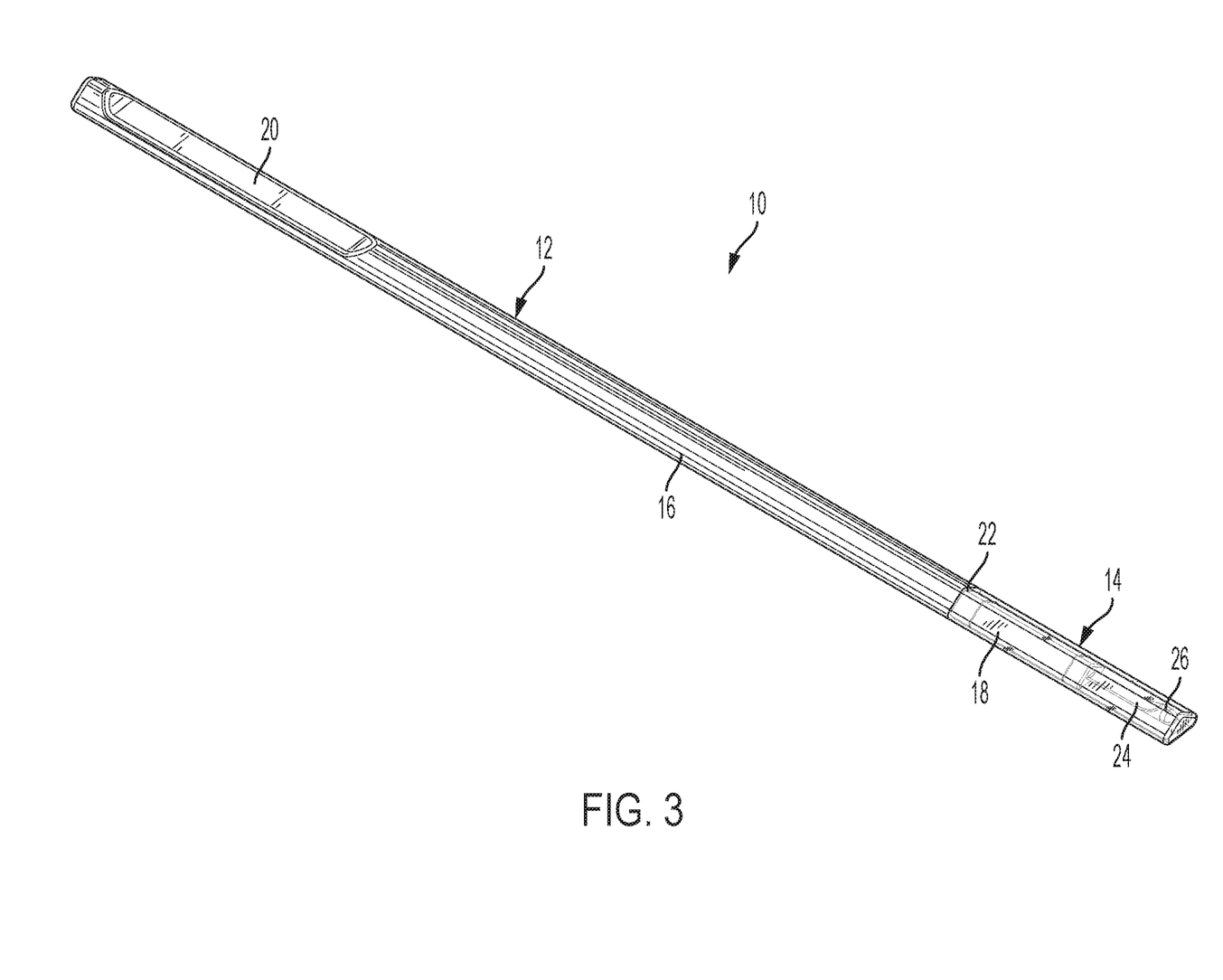
FIG. 3 is a top perspective view of the exemplary vitrification stick.
Figure 4:
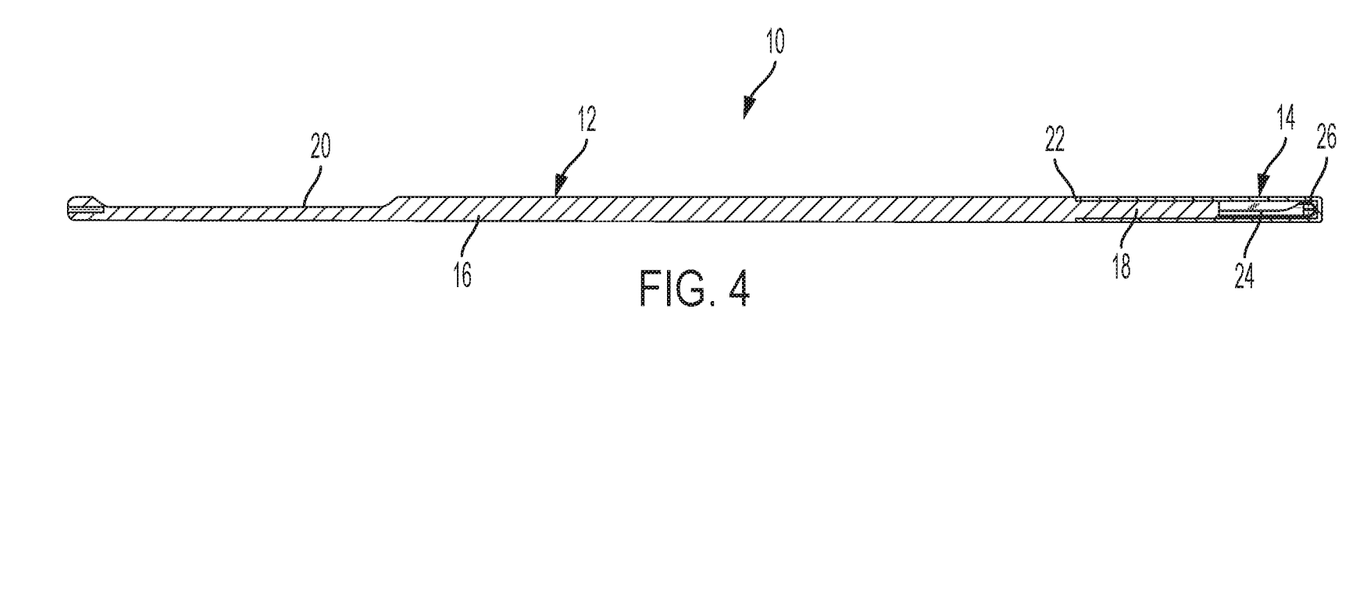
FIG. 4 is cross-sectional view of the exemplary vitrification stick taken along line 4-4 from FIG. 1.
Figure 5:
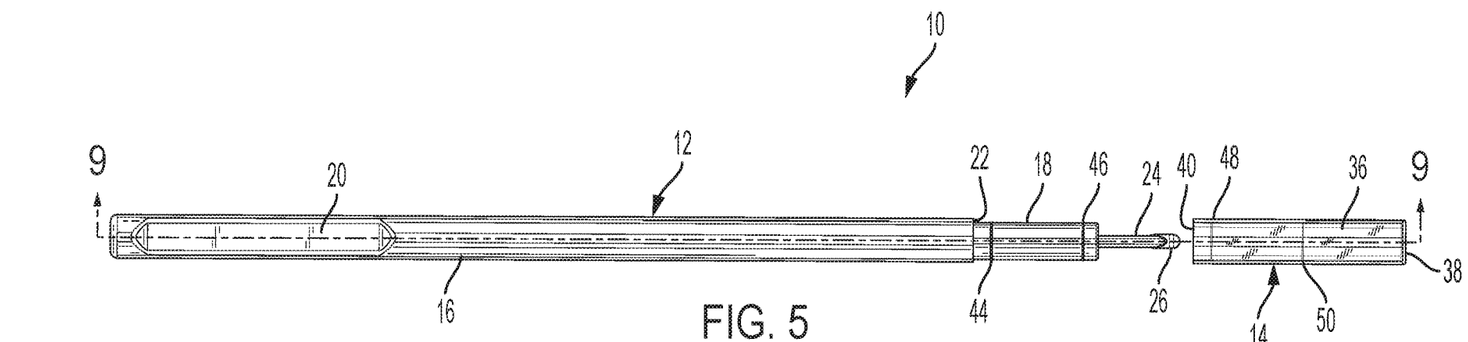
FIG. 5 is an exploded top plan view of the exemplary vitrification stick.
Figure 6:
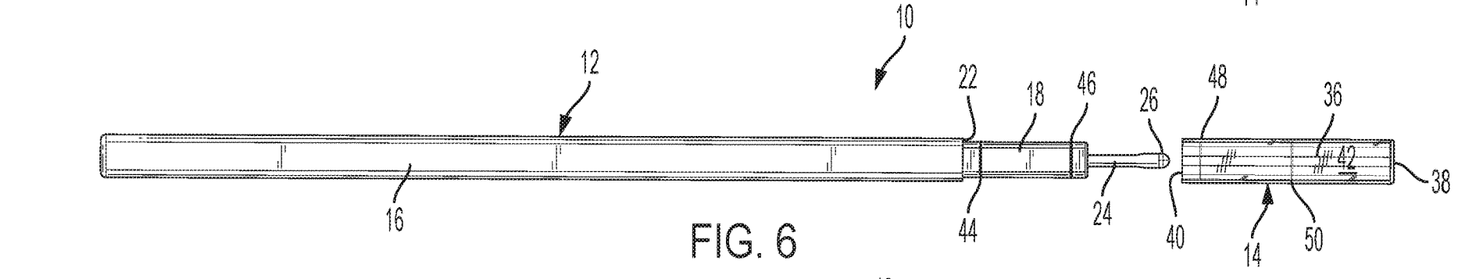
FIG. 6 is an exploded bottom plan view of the exemplary vitrification stick.
Figure 7:
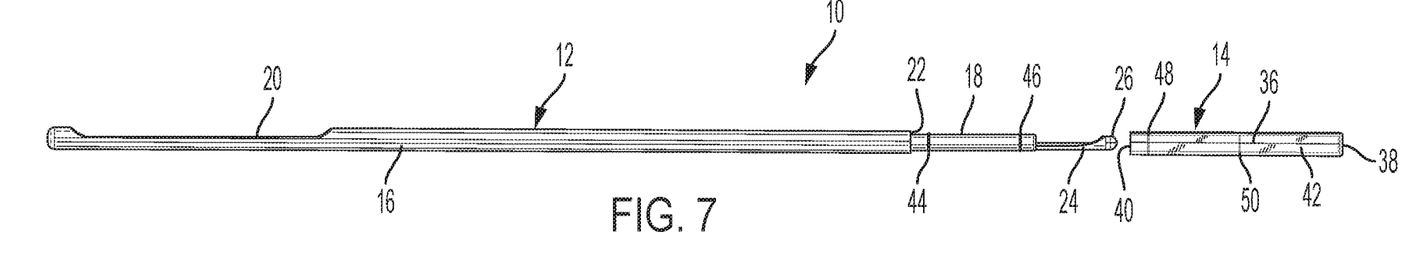
FIG. 7 is an exploded right side view of the exemplary vitrification stick.
Figure 8:
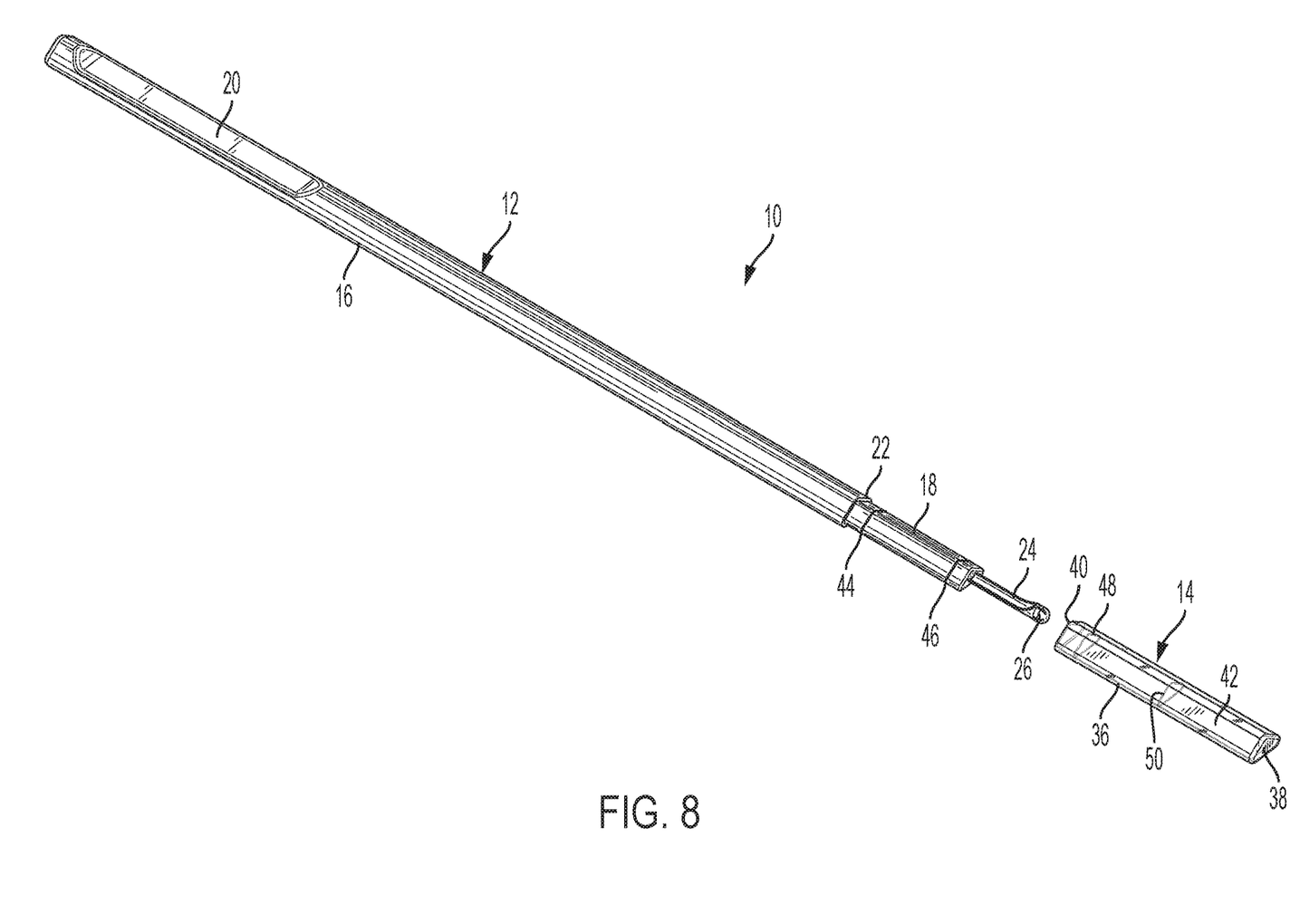
FIG. 8 is an exploded top isometric view the exemplary vitrification stick.
Figure 9:
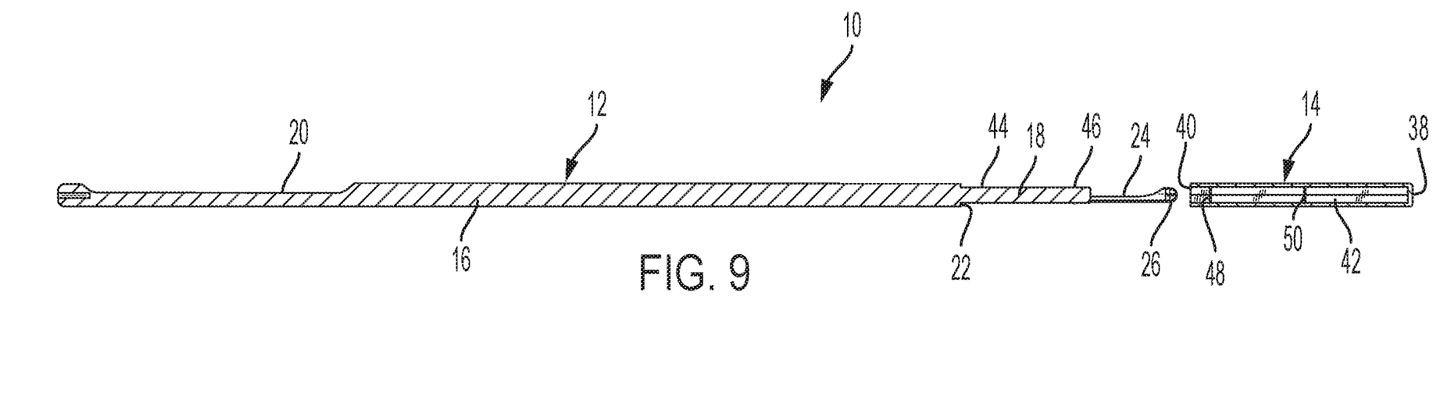
FIG. 9 is an exploded cross-sectional view of the exemplary vitrification stick taken along line 9-9 from FIG. 5.
Figure 10:
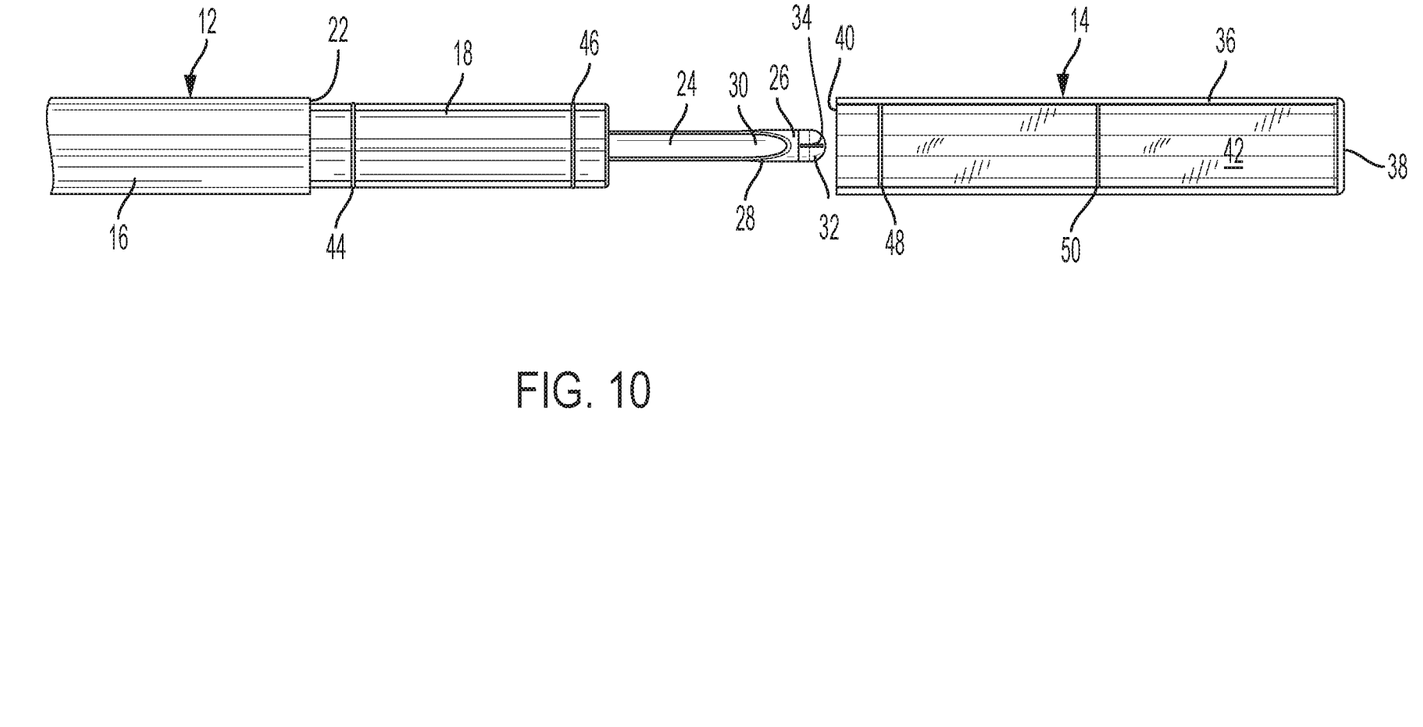
FIG. 10 is an enlarged view of the exemplary vitrification stick from FIG. 5.
Figure 11:
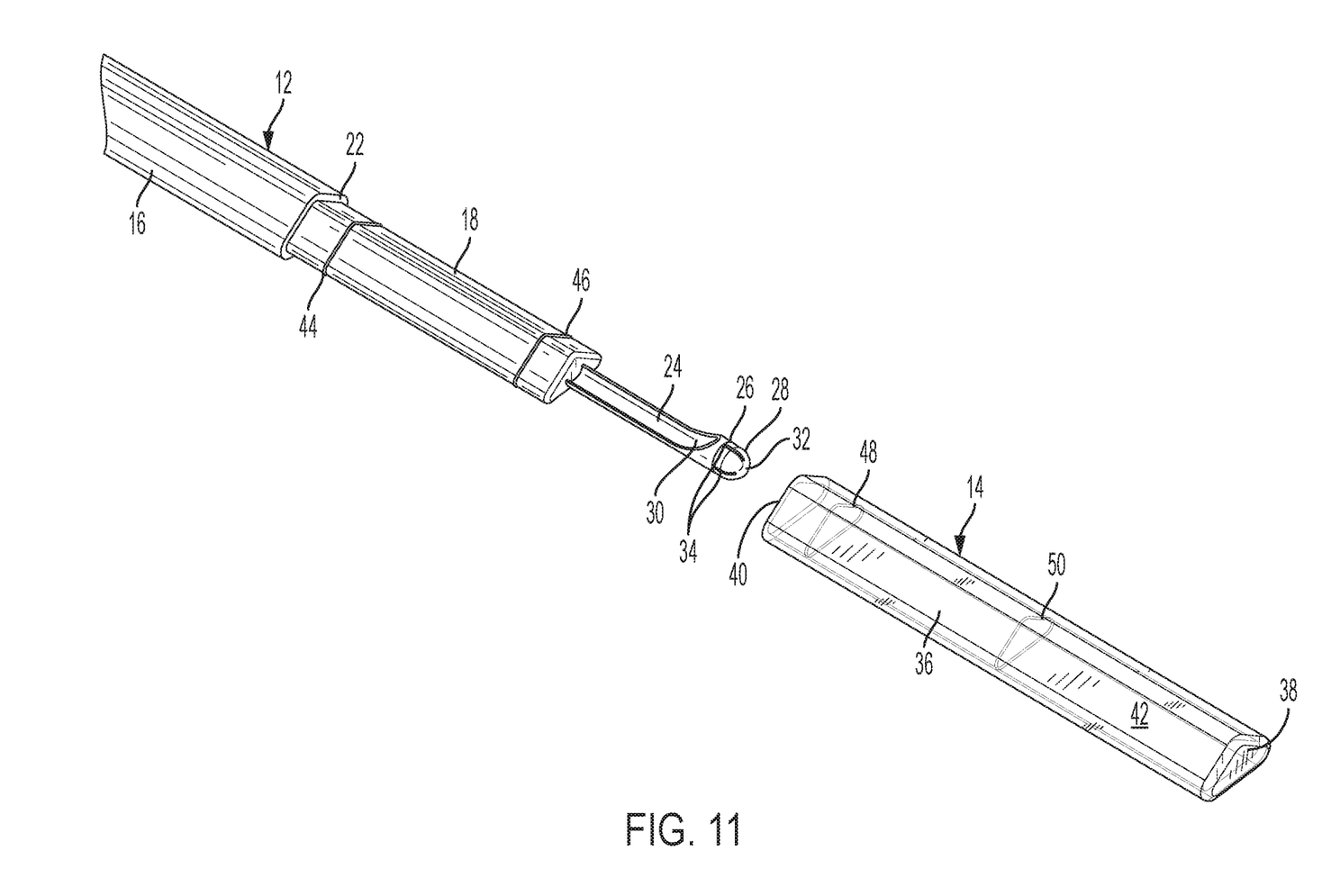
FIG. 11 is an enlarged view of the exemplary vitrification stick from FIG. 8.
Figure 12:
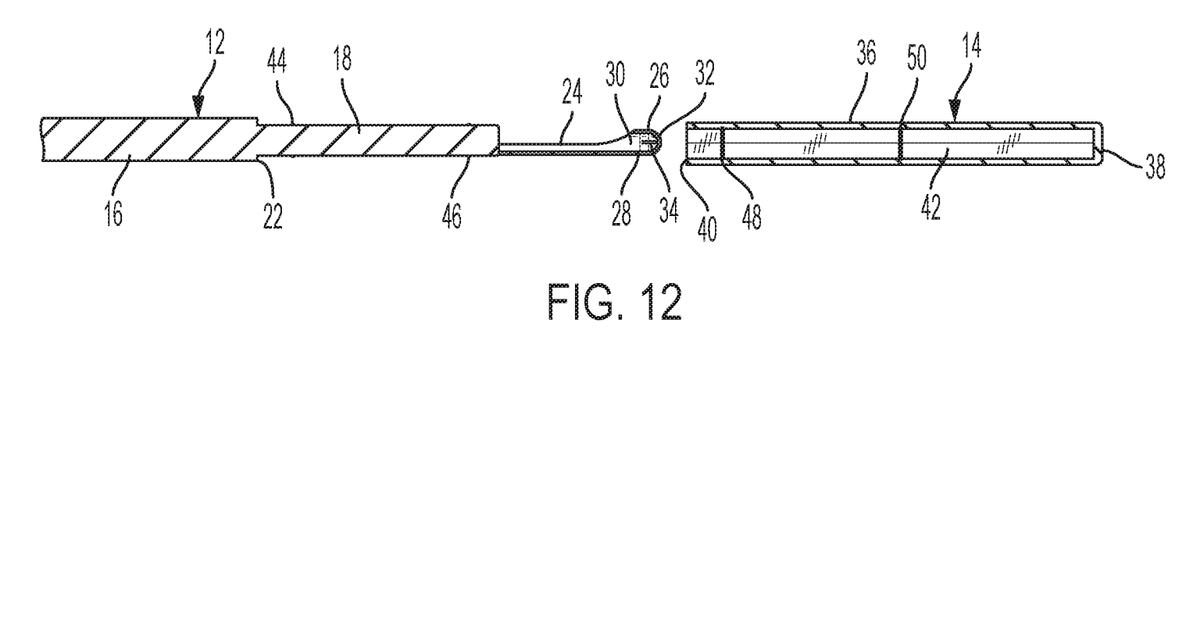
FIG. 12 is an enlarged view of the exemplary vitrification stick from FIG. 9.

Referring now particularly to FIGS. 10-12, the operation and use of the exemplary vitrification stick 10 according to an aspect of the present invention will be discussed. The specimen of biological material to be cryopreserved, for example a human egg or embryo, may be inserted into the interior region 30 of the basket end tip 26 through known techniques, for example through the use of a pipette. The biological material may then be placed on the shell 32 and/or peripheral wall 28 so that the biological material is substantially enclosed within the basket end tip 26. A cryoprotectant fluid may then be applied into the basket end tip 26 or onto the specimen end 24 so that it flows over the biological material, and then out of the one or more slots 34. The one or more slots 34 may be sized and/or dimensioned so that a predetermined volume of the cryoprotectant fluid remains in contact with the biological material at certain amount of time prior to being evacuated out of the one or more slots 34. Furthermore, the predetermined volume of the cryoprotectant fluid may be of a volume that does not flow out of the basket end tip 26 in the direction towards the specimen end 24, so that the risk of the biological material being washed away from the vitrification stick 10 is reduced. A further cryoprotectant fluid may then be applied into the basket end tip 26 or onto the specimen end 24 in the same manner until the desired vitrification and cryopreservation of the biological material is achieved. Alternatively, the basket end tip 26 of the vitrification stick 10 may be dipped into the cryoprotectant fluid so that the cryoprotectant fluid enters the basket end 26 through the one or more slots 34. The basket end tip 26 may then be removed from the cryoprotectant fluid so that the cryoprotectant fluid drains back out from the one or more slots 34. Preferably, the basket end tip 26 may only be dipped into the cryoprotectant fluid up to the height of the lowest part of the peripheral wall 28 in order to reduce the risk that the biological material is accidentally released from the basket end tip 26.

The body 12 and the cap 14 of the vitrification stick 10 may be made from a suitable rigid material that is nonreactive to any ingredients of the cryoprotectant fluids, and suitable for maintaining its structural integrity at cryogenic temperatures. For example, various polymers, such as polyester, polyolefin, polyethylene, polypropylene, ethylene-vinyl acetate copolymer, styrene resin, polystyrene, polyamide, or medical grade polystyrene crystal may be used for the body and the cap 14. As illustrated by the exemplary embodiment of the vitrification stick 10 shown in FIGS. 1-12, the cap 14 may be constructed of a transparent material. However, it is understood that the cap 14 may also be made from a translucent or opaque material, and may be the same or different from the body 12.

Figure 13:
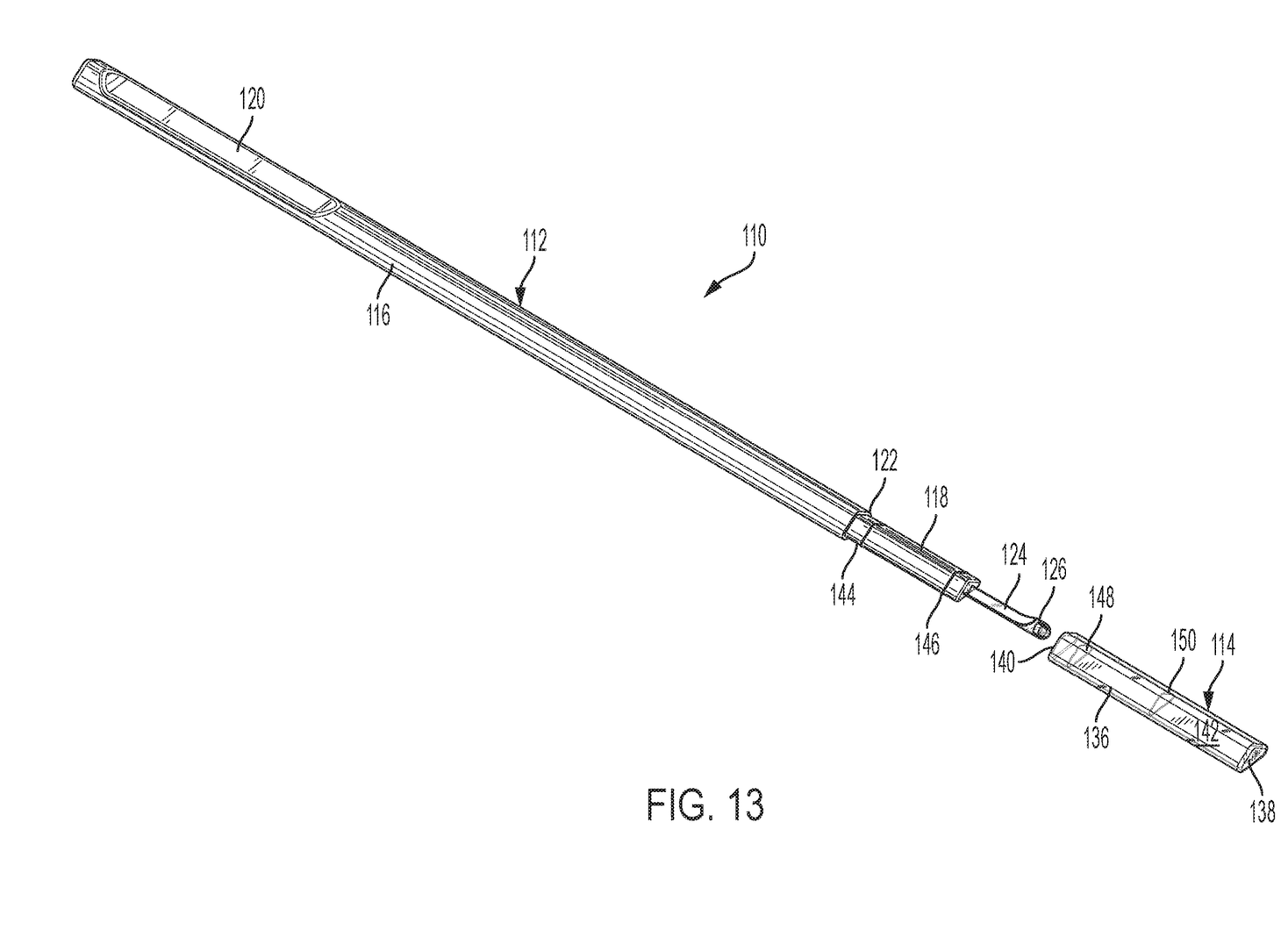
FIG. 13 is an isometric view of another exemplary vitrification stick according to another aspect of the present invention.
Figure 14:
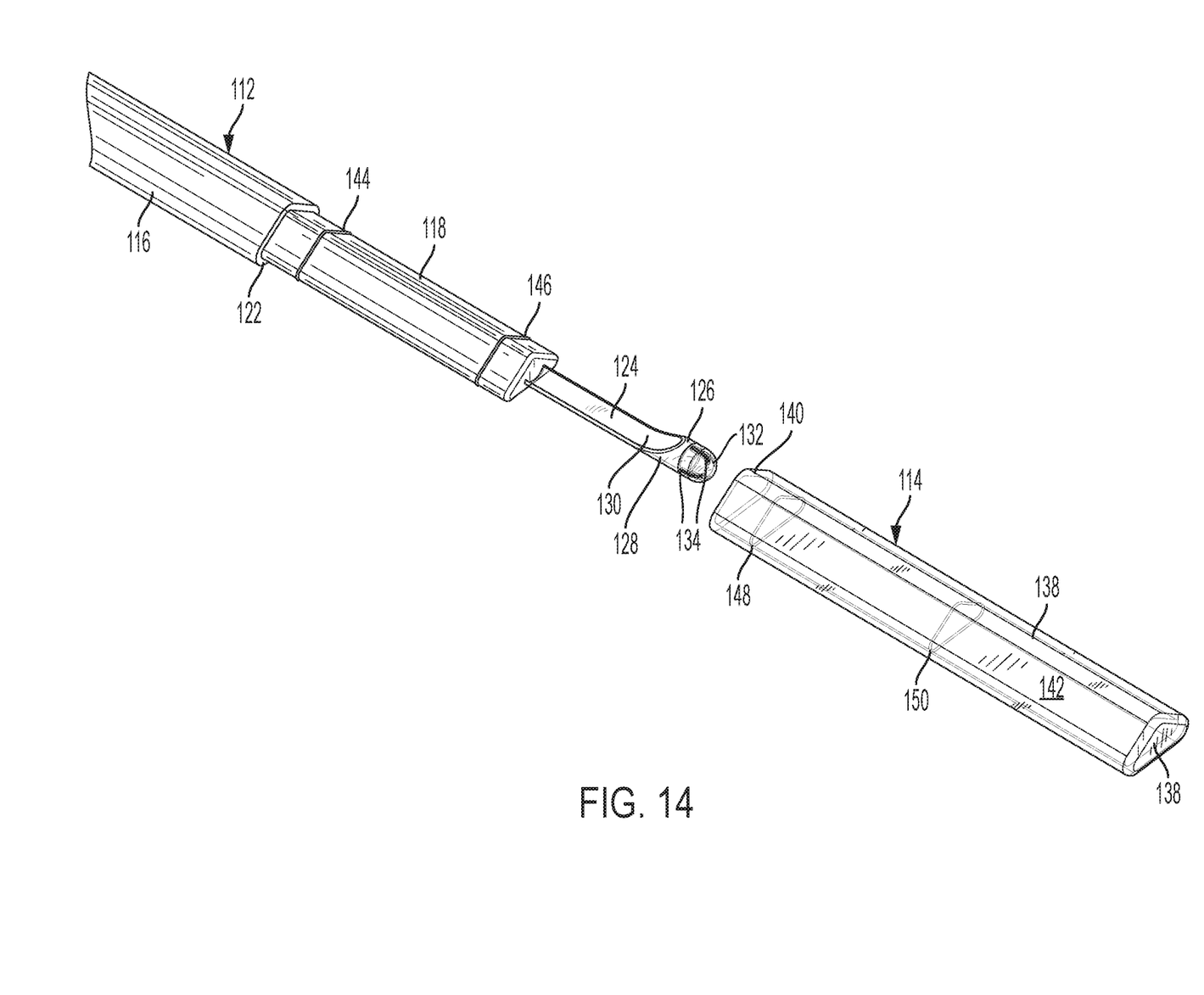
FIG. 14 is an enlarged view of the other exemplary vitrification stick from FIG. 13.

Referring now to FIGS. 13 and 14, therein illustrated in another exemplary embodiment of a vitrification stick, generally referred to as 110, according to the present invention. In this exemplary embodiment, a portion of the body 112 of the vitrification stick 110, namely the specimen end 124 and basket end tip 126 are made from a transparent material, for example a transparent polymer. Constructing at least the specimen end 124 and the basket end tip 126 from a transparent material facilitates insertion and processing of the biological materials within the basket end tip 126. The vitrification stick 110 in this exemplary embodiment may also include a cap 114, a first portion 116 of the body 112 and a second portion 118 of the body 112. The body 112 may also include a handle 120, and a shoulder 122 may separate the first portion 116 from the second portion 118. The basket end tip 126 may include a peripheral wall 128 enclosing an interior region 130, and a shell 132 having one or more slots 134 formed therein. The cap 114 may include one or more walls 136, a closed end 138 and an open end 140 defining an interior region 142. The cap 114 may be secured to the body 112 by cooperating first 144 and second ribs 146 disposed on the second portion 118 of the body 112 and first 148 and second grooves 150 formed in the cap 114. The vitrification stick 110 may be constructed of the same or similar materials as the vitrification stick 10, and may be operated and used in the same or similar manner as the vitrification stick 10.

It will thus be seen that the objects set forth above, among those made apparent from the preceding description, are efficiently attained and, since certain changes may be made in the above article without departing from the scope of this invention, it is intended that all matter contained in this disclosure or shown in the accompanying drawings, shall be interpreted, as illustrative and not in a limiting sense. It is to be understood that all of the present figures, and the accompanying narrative discussions of corresponding embodiments, do not purport to be completely rigorous treatments of the invention under consideration. It is to be understood that the above-described arrangements are only illustrative of the application of the principles of the present invention. Numerous modifications and alternative arrangements may be devised by those skilled in the art without departing from the scope of the present invention.

What is claimed is:

1. A vitrification stick, comprising:
a body having a first portion and a second portion; and
a specimen end extending from the second portion of the body, and having a basket end tip formed thereon;
wherein the basket end tip comprises a peripheral wall enclosing an interior region of the basket end tip; and
wherein the basket end tip further comprises a shell connected to the peripheral wall and enclosing the interior region on a first side, and the interior region is open on a second side in a direction towards the second portion of the body.

2. The vitrification stick according to claim 1, wherein the shell comprises at least one slot formed therein, and the at least one slot exposes the interior region of the basket end tip to an area external to the basket end tip.

3. The vitrification stick according to claim 2, wherein the at least one slot extends into at least a portion of the peripheral wall.

4. The vitrification stick according to claim 1, wherein the second portion has a smaller cross-sectional dimensional size than the first portion, and a shoulder is positioned between the first portion and the second portion.

5. The vitrification stick according to claim 4, wherein the second portion of the body comprises a first rib positioned adjacent to the shoulder and extending at least partially around a perimeter of the second portion, and a second rib positioned adjacent to the specimen end and extending at least partially around the perimeter of the second portion.

6. The vitrification stick according to claim 1, further comprising a cap configured to receive at least the specimen end, and wherein the cap comprises an open end and a closed end, and a plurality of walls defining a hollow interior chamber extending between the open end and the closed end.

7. The vitrification stick according to claim 6, wherein the cap is dimensioned so as to receive the specimen end and at least a part of the second portion of the body.

8. The vitrification stick according to claim 6, wherein the second portion has a smaller cross-sectional dimensional size than the first portion, and a shoulder is positioned between the first portion and the second portion, wherein the second portion of the body comprises a first rib positioned adjacent to the shoulder and extending at least partially around a perimeter of the second portion, and a second rib positioned adjacent to the specimen end and extending at least partially around the perimeter of the second portion.

9. The vitrification stick according to claim 8, wherein the cap further comprises a first groove extending at least partially around the hollow interior chamber, and a second groove extending at least partially around the hollow interior chamber.

10. The vitrification stick according to claim 9, wherein the first groove is configured for engagement with the first rib and the second rib, and wherein the second groove is configured for engagement with the second rib, and
wherein as a result of the engagement of the second groove with the second rib, the basket end is sealed within the hollow interior chamber of the cap.

11. The vitrification stick according to claim 1, wherein the vitrification stick is comprised of a material selected from the group consisting of polyester, polyolefin, polyethylene, polypropylene, ethylene-vinyl acetate copolymer, styrene resin, polystyrene, polyamide, and medical grade polystyrene crystal.

12. The vitrification stick according to claim 1, wherein the basket end tip is comprised of a transparent material.

13. The vitrification stick according to claim 12, wherein the transparent material is a polymer.

14. The vitrification stick according to claim 1, wherein the interior region of the basket end tip is dimensioned to receive and retain a human egg or a human embryo.

15. The vitrification stick according to claim 1, wherein the specimen end comprises a thin connector positioned between the basket end tip and the second portion of the body.

16. The vitrification stick according to claim 15, wherein at least one side of the peripheral wall adjacent to the thin connector has a first height, and a side of the peripheral wall opposite the thin connector has a second height, and wherein the second height is less than the first height.

17. The vitrification stick according to claim 16, wherein the peripheral wall at a first location along the peripheral wall adjacent to the thin connector tapers from the first height down to the second height at a second location along the peripheral wall opposite the thin connector, and then back to the first height at a third location along the peripheral wall adjacent to the thin connector.

* * * * *